United States Patent [19]

Miura et al.

[11] Patent Number: 4,857,792
[45] Date of Patent: Aug. 15, 1989

[54] CIRCULAR DIRECTION VIBRATOR

[75] Inventors: Shinsuke Miura; Susumu Ishizuka; Setsuo Kojima, all of Tokyo, Japan

[73] Assignee: Yamaichi Electric Mfg. Ltd., Tokyo, Japan

[21] Appl. No.: 173,638

[22] Filed: Mar. 25, 1988

[30] Foreign Application Priority Data

Apr. 30, 1987 [JP] Japan ................................. 62-107390

[51] Int. Cl.$^4$ ........................................... H01L 41/08
[52] U.S. Cl. .................................... 310/323; 310/328; 310/331; 310/332
[58] Field of Search ................. 310/328, 323, 330–333

[56] References Cited

U.S. PATENT DOCUMENTS

| 2,488,586 | 11/1949 | Diemer ........................... | 310/333 X |
| 4,019,073 | 4/1977 | Vishnevsky et al. ............ | 310/323 X |
| 4,399,386 | 8/1983 | Osaka et al. .................... | 310/331 X |
| 4,742,260 | 5/1988 | Shimizu et al. ................. | 310/331 X |

FOREIGN PATENT DOCUMENTS 0686155   9/1979   U.S.S.R. ............................. 310/333

*Primary Examiner*—Mark O. Budd
*Attorney, Agent, or Firm*—Wenderoth, Lind & Ponack Co.

[57] ABSTRACT

A circular direction vibrator has a pair of piezoelectric bimorph type vibrators, and a carrier member serving as a fulcrum of a circular direction vibration shaft and adapted to support the vibrators in a cantilever fashion, the pair of vibrators extending in opposite directions with respect to each other from the carrier member and the vibrators connected in such a manner as to generate the same phase voltage when vibrating in a circular direction.

4 Claims, 2 Drawing Sheets

CIRCULAR DIRECTION VIBRATOR

BACKGROUND OF THE INVENTION

1. Field of the Invention

This invention relates to a circular direction vibrator in which a piezoelectric bimorph type vibrator is employed.

2. Description of the Prior Art

A piezoelectric bimorph type vibrator is known comprising a bimorph cell composed of a piezoelectric ceramic member and a metal plate attached thereto for converting a vibration in a lengthwise direction to a mechanical vibration in a direction of thickness of the bimorph utilizing the characteristic of the piezoelectric ceramic which is vibrated in a lengthwise direction when a voltage is applied thereto. There has also been provided a piezoelectric bimorph type vibrator in which the conversion of electrical energy into mechanical vibration in a direction of thickness of the bimorph can be obtained by attaching two piezoelectric ceramic members together so that the elongation and contraction directions of one of the members are opposite to those of the other of the members when a voltage is applied to the members causing each of the members to alternately elongate and contract. In either case, the piezoelectric ceramic member is obtained by subjecting ferroelectric ceramics capable of spontaneous polarization to polarization treatment (poling) which comprises applying high voltage to ferroelectric ceramics so as to induce one polarization direction therein. The polarization treatment has been effected merely for the purpose of inducing a single polarization direction in a single ceramic body.

Since the vibrating action of the conventional piezoelectric bimorph type vibrators is a simple bending motion produced when a voltage is applied thereto, the use of the conventional piezoelectric bimorph type vibrators producing such a bending motion as a vibration source is limited to electroacoustic transducers and piezoelectric filters, for example.

In general, the conventional piezoelectric vibrators have limited vibration modes in a direction of thickness and in a diametrical direction and these vibration modes are usually used as a direct drive.

SUMMARY OF THE INVENTION

It is therefore an object of the present invention to provide a circular direction vibrator, in which a favorable circular direction vibration is generated by utilizing a piezoelectric bimorph type vibrator which produces the aforementionend bending motion.

Another object of the present invention is to provide a circular direction vibrator in which the piezoelectric ceramics can be used in a new field utilizing the circular direction vibration mode as a driving mode or a detecting mode and which is suitably used, for example, in a viscosity detector or a density meter.

A further object of the present invention is to provide a circular direction vibrator which can be suitably used as a driving source or a detecting source (vibration sensor) of a density meter or a viscosity meter, and which can obviate problems such as those created when a conventional vibrator is used as a driving source. These problems arise when vibration is transmitted to a detector to cause the detector to be vibrated in the same direction in a measuring liquid so that the density or viscosity of the liquid can be detected from the changes in the vibration of the detector resulting in a vibrating wave produced by the detector that propagates in the liquid to create wave motion which disturbs the measurement taken. Therefore, a highly accurate measurement is difficult to obtain and in addition, the measuring range is limited.

In order to achieve the above object, there is essentially provided a circular direction vibrator comprising a pair of piezoelectric bimorph type vibrators, and a carrier member serving as a fulcrum of a circuit direction vibration shaft and adapted to support said vibrators in a cantilever fashion, said pair of vibrators extending in opposite directions with respect to each other from said carrier member, and said vibrators connected in such a manner as to generate the same phase voltage when vibrating in the circular direction.

According to the present invention, during circular direction vibration about the circular direction vibrating shaft of the carrier member, i.e. repetitive motion in a clockwise direction and in a counterclockwise direction, the free ends of the pair of vibrators supported on the carrier member in a cantilever fashion are vibrated in the directions of thickness thereof but in opposite directions with respect to each other. As a result, a positive voltage (or a negative voltage) having the same phase is generated in the pair of piezoelectric bimorph type vibrators and an output signal is obtained.

Further, if vibration other than the circular direction vibration about the carrier member is imparted to the carrier member and the pair of vibrators, for example if the pair of vibrators are vibrated to produce bending motion in the same directions of thickness, a voltage having an opposite phase is produced in which a positive voltage is produced in one vibrator and a negative voltage is produced in the other vibrator, and as a result, these voltages offset and the output is zero.

Accordingly, in the circular direction vibrator according to the present invention, a normal electric output can be obtained only when a circular direction vibration is imparted thereto.

Although mechanical motion (circular direction vibration) is converted into electric energy (voltage output) according to the foregoing description, in view of the electric/mechanic converting function of the piezoelectric bimorph type vibrator, a conversion of electric energy to mechanical motion can of course be obtained. That is, when a voltage is applied to the circular direction vibrator, since the basic ends of the pair of piezoelectric bimorph type vibrators are secured to the carrier member in a cantilever-supporting fashion, the free end of one vibrator vibrates in one direction of thickness, whereas the free end of the other vibrator vibrates in an opposite direction of thickness. That is, circular direction vibration about the carrier member can be obtained.

In the present invention, the above-mentioned circular direction vibrator can be easily formed as a combination of the bimorph type vibrators. In addition, a circular direction vibrator which has a simple structure and a proper vibrating orbit can be assuredly realized.

As already described, the vibrating mode of the circular direction vibrator can be suitably used as a driving mode or a detecting mode (vibration sensor) when the viscosity or density of the liquid is to be measured.

The above and other objects and attendant advantages of the present invention will be apparent to those skilled in the art from a reading of the following description and claims in conjunction with the accompanying drawings which constitute part of the present specification.

BRIEF DESCRIPTION OF THE DRAWINGS

The drawings illustrate preferred embodiments of the present invention, wherein.

DETAILED DESCRIPTION OF THE PREFERRED EMBODIMENTS

Figure 1:
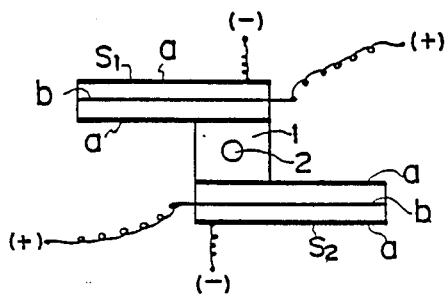
FIG. 1 is a plan view of a circular direction vibrator according to the present invention.

The preferred embodiment of the present invention will be described hereunder with reference to FIGS. 1 through 5.

As described above, a circular direction vibrator comprises a pair of right and left piezoelectric bimorph type vibrators $S_1$ and $S_2$.

The vibrators $S_1$ and $S_2$ are bimorphs of piezoelectric ceramics as illustrated, or bimorphs of a piezoelectric ceramic and a vibrating plate (metal plate). Reference character a denotes outside electrodes disposed on the outer peripheral surfaces of the piezoelectric bimorph type vibrators $S_1$ and $S_2$, reference character b denotes intermediate electrodes disposed intermediate the laminated surfaces, and reference numeral 2 denotes a circular direction vibrating shaft of a carrier member 1 and therefore of a circular direction vibrator.

The vibrators $S_1$ and $S_2$ are symmetrically mounted on the carrier member 1 serving as the circular direction vibrating shaft fulcrum.

One symmetrical arrangement of the vibrators $S_1$ and $S_2$ is shown in FIG. 1 in which a rectangular carrier member 1 has the circular direction vibrating shaft 2 disposed at its center, and a basic end of one vibrator $S_1$ is disposed on one of the opposite side surfaces of the carrier member 1 parallel to the electrodes, whereas the basic end of the other vibrator $S_2$ is disposed on the other side surface parallel to the electrodes, the pair of vibrators $S_1$ and $S_2$ extending in opposite directions with respect to each other.

Figure 2:
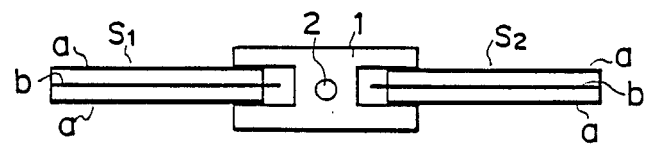
FIG. 2 is a plan view of another example of a circular direction vibrator.

As shown in FIG. 2, the pair of vibrators $S_1$ and $S_2$ are disposed on the carrier member 1 such that the pair of vibrators $S_1$ and $S_2$ extend symmetrically along the same linear line.

That is, the pair of vibrators $S_1$ and $S_2$ are mounted to the carrier member 1 in a cantilever fashion and extend in opposite directions from the carrier member 1 to free ends thereof. The term "shaft symmetry arrangement" when used herein refers to the above mentioned arrangement. The pair of vibrators $S_1$ and $S_2$ are mounted on the carrier member 1 in a cantilever fashion and vibrated at their free ends.

Figure 3:
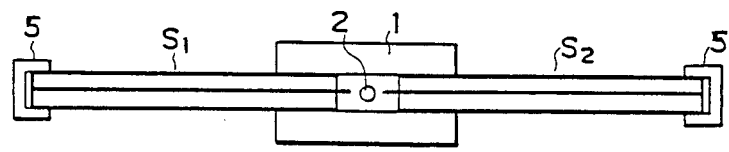
FIG. 3 is a plan view of still another example of a circular direction vibrator.

In one preferred embodiment, as shown in FIG. 3, inertial massive members 5 are attached to the free ends of the vibrators $S_1$ and $S_2$ in order to establish the vibrating frequency (e.g., establish a resonance frequency of the vibrating system).

Such arranged vibrators $S_1$ and $S_2$ have the electrodes connected such that when vibrating in the same direction of thickness, opposite phase voltages are generated, whereas when vibrating in opposite directions of thickness (when vibrating in the circular direction) about the circular direction vibrating shaft 2 of the carrier member 1, the same phase voltages are generated. In other words, when the voltages are applied, the free ends of the vibrators $S_1$ and $S_2$ are vibrated in the opposite directions of thickness with respect to each other so as to impart a circular direction vibration.

The expression "the same direction of thickness vibration" means that the free ends of the pair of vibrators $S_1$ and $S_2$ are simultaneously vibrated in the direction as shown by arrow $X_1$ of FIG. 4 wherein the cantilever carrier member 1 acts as a fulcrum, whereas the expression "the opposite directions of thickness vibration" means that the free end of one vibrator $S_1$ is vibrated in one direction of thickness (e.g., the direction indicated by $X_1$ in FIG. 4), while the other vibrator $S_2$ is vibrated in the other direction of thickness (e.g., the direction indicated by $X_2$ in FIG. 4). In other words, it means that they collectively vibrate in a circular direction.

Several examples of the electrode connection of the vibrators $S_1$ and $S_2$ are described with reference with FIGS. 4A through 4D.

Figure 4A:
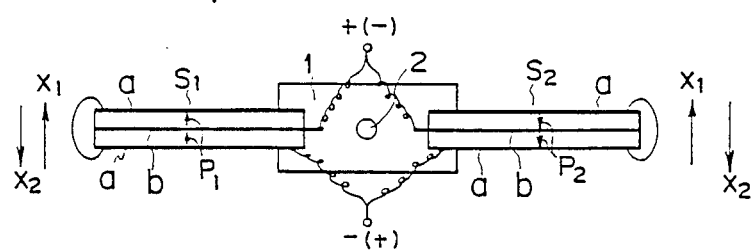
FIGS. 4A through 4D are plan views showing examples of operative connections of the elements of the circular direction vibrator.

FIG. 4A illustrates one example of a circular direction vibrator in which the piezoelectric bimorph vibrators $S_1$ and $S_2$ are connected in parallel. As is shown, the vibrators $S_1$ and $S_2$ are laminated and the polarizing directions $P_1$ and $P_2$ are oriented in the same direction in the respective vibrators. Moreover, the vibrators $S_1$ and $S_2$ are mounted on the carrier member 1 in a cantilever fashion, and the intermediate electrodes b and the outside electrodes a are connected with each other, respectively, one connecting end being a positive voltage terminal (or a negative voltage terminal) and the other connecting end being a negative voltage terminal (or a positive voltage terminal).

In the foregoing arrangement, when vibration in the same direction of thickness $X_1$ or $X_2$ is simultaneously applied to the pair of vibrators $S_1$ and $S_2$, a positive voltage is generated in the intermediate electrode b of one of the vibrators $S_1$ and $S_2$ and a negative voltage is generated in the other intermediate electrode b. As a result, the positive and negative voltages offset each other. Similarly, a positive voltage is generated in the outside electrodes a of one of the vibrators $S_1$ and $S_2$, whereas a negative voltage is generated in the other outside electrodes a. As a result, these positive and negative voltages offset each other. Accordingly, the output between the positive voltage terminal (+) and the negative voltage terminal (−) becomes zero.

That is, the circular direction vibrators do not generate an output under any vibration other than in the circular direction.

On the other hand, when a circular direction vibration is applied to the carrier member supporting the vibrators $S_1$ and $S_2$ in a cantilever fashion about the circular direction vibrating shaft 2, the free end of one of the vibrators $S_1$ and $S_2$ is vibrated in one direction of thickness $X_1$ and the free end of the other vibrator is vibrated in the other direction of thickness, i.e., the free ends of the vibrators $S_1$ and $S_2$ are vibrated in opposite directions of thickness with respect to each other (circular direction vibration). As a result, a positive voltage (or a negative voltage) having the same phase is generated in the outside electrodes a of the vibrators $S_1$ and $S_2$, and a negative voltage (or a positive voltage) having the same phase is generated in the intermediate electrodes b. As a result, a voltage output is generated between the positive voltage terminal (+) and the negative voltage terminal (−). When a predetermined voltage is applied to the pair of vibrators $S_1$ and $S_2$, an opposite effect occurs with respect to the foregoing effect, i.e. a circular direction vibration is obtainable as an output due to the electric/mechanic converting function of the piezoelectric bimorph type vibrators $S_1$ and $S_2$.

Figure 4B:
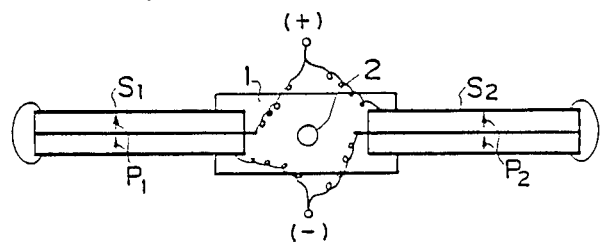

FIG. 4B illustrates another example in which the vibrators $S_1$ and $S_2$ have the same polarizing direction as that of FIG. A and the vibrators are connected in series. That is, in the pair of vibrators $S_1$ and $S_2$, the outside electrodes a of each vibrator are connected to each other at first ends thereof and one outside electrode a of each vibrator is connected at the second end thereof with the intermediate electrode b of the other vibrator to create a positive voltage terminal and a negative voltage terminal. In this case, in accordance with the same principle as that described above, a positive voltage (or a negative voltage) is generated in one connecting terminal of the outside electrodes a of one vibrator and the intermediate electrode b of the other vibrator, whereas a negative voltage (or a positive voltage) is generated in the other connecting terminal when a circular direction vibration is applied to the vibrators. Likewise, when a vibration other than the circular direction vibration is applied to the vibrators, an offset voltage having an opposite phase is generated in the outside electrodes a of one vibrator and the intermediate electrode b of the other vibrator, and as a result, the output is zero. On the contrary, when a voltage is imparted to the electrodes, a mechanical circular direction vibration output is obtainable in the same way as mentioned above.

Figure 4C:
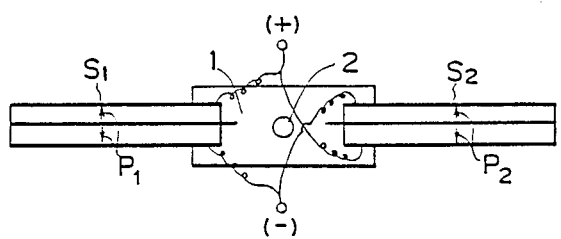

In FIG. 4C, one vibrator $S_1$ has a piezoelectric bimorph in which the polarizing directions $P_1$ are oriented outward with respect to each other, whereas the other vibrator $S_2$ has piezoelectric bimorph in which the polarizing directions $P_2$ are oriented inward with respect to each other. Further, one outside electrode a of one vibrator $S_1$ and the opposite outside electrode a of the other vibrator $S_2$ are connected with the positive voltage terminals, whereas the other outside electrode a of vibrator $S_1$ and the opposite outside electrode a of the vibrator $S_2$ are connected with the negative voltage terminals so as to realize a series connection.

In this case, in accordance with the same acting principle as mentioned above, when a circular direction vibration is applied, a positive voltage (or a negative voltage) is generated at the connecting terminals of one pair of connected outside electrodes a, whereas a negative voltage (or a positive voltage) is generated in the other connecting terminals. Likewise, when vibration other than circular direction vibration is applied to the vibrators, an offset voltage having an opposite phase is generated in each outside electrode a of one vibrator and the outside electrode a of the other vibrator connected thereto, and as a result, the output becomes zero. On the contrary, when a voltage is imparted to the vibrators, they are vibrated in the circular direction in the same way as mentioned above.

Figure 4D:
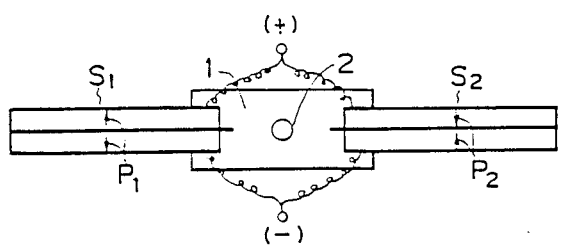

FIG. 4D illustrates still another embodiment in which the vibrators $S_1$ and $S_2$ have the same polarizing direction as that of FIG. 4C, and one outside electrode a of each of the vibrators $S_1$ and $S_2$ is connected with a positive voltage terminal + (or a negative voltage terminal), whereas the other outside electrode a of each of the vibrators $S_1$ and $S_2$ is connected with the negative voltage terminal—(or the positive voltage terminal) so as to realize a series connection.

In this case, in accordance with the same acting principle as that mentioned above, when a circular direction vibration is applied to the vibrators, a positive voltage (or a negative voltage) is generated in the connecting terminal at which one outside electrode a of each of the vibrators is connected, whereas a negative voltage (or a positive voltage) is generated in the other connecting terminal. Further, when vibration other than the circular direction vibration is applied to the vibrators, an offset voltage having an opposite phase is generated in each pair of the connected outside electrodes a of the vibrators, and as a result, the output becomes zero.

The embodiments shown in FIGS. 4A through 4D operate under the same principle and differ in structure only with respect to the connecting state between the piezoelectric bimorph type vibrators $S_1$ and $S_2$, and the orientation of the polarizing directions.

Figure 5:
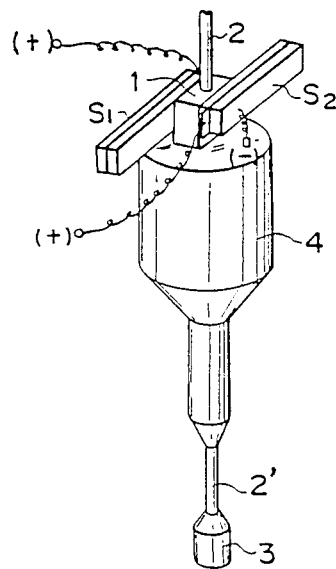
FIG. 5 is a perspective view of a detecting portion of a density meter or a viscosity meter with the circular direction vibrator applied thereto.

FIG. 5 illustrates one example in which a circular direction vibrator comprising the pair of piezoelectric bimorph type vibrators $S_1$ and $S_2$ is applied to a density meter or a viscosity meter.

As illustrated, the vibrating shaft 2 of the carrier member 1 and its vibration transmitting shaft 2' are connected in such a manner as to have the same vibrating axis. The circular direction vibrators are mounted on the vibration transmitting shaft 2'. A detecting terminal 3 to be dipped in liquid is mounted on the front end of the vibration transmitting shaft 2'. If necessary, an inertial mass 4 for establishing the resonance frequency is integrally mounted on the vibration transmitting shaft 2'.

In one example of the above-mentioned embodiment, the circular direction vibration sensor is driven to cause the detecting terminal 3 to be vibrated in the circular direction in the measuring liquid. Further, the vibration of the detecting terminal 3 in the measuring liquid is fed back to the same circular direction vibrator in order to produce an electric signal corresponding to the changes in vibration of the detecting terminal. In another example, the detecting terminal 3 is vibrated in the circular direction by a separate driving source, and the vibration of the detecting terminal 3 in the liquid is detected by the circular direction vibrator. In either case, the circular direction vibrators function as vibration sensors, i.e. angular acceleration sensors and output an electric signal only when the detecting terminal is vibrated in the circular direction to detect the density or the viscosity of the liquid with a high degree of reliability.

According to the present invention, during circular direction vibration about the circular direction vibrating shaft, the free ends of the pair of vibrators supported by the carrier member in a cantilever fashion are vibrated in the opposite directions of thickness (circular direction vibration) with respect to each other without fail, and a positive voltage (or a negative voltage) having the same phase is generated in the pair of piezoelectric bimorph type vibrators without fail, and as a result, a voltage output can be obtained.

If vibration other than the circular direction vibration about the carrier member, such as for example a vibration in which the pair of vibrators produce bending motion in the same directions of thickness, is imparted to the carrier member and the pair of piezoelectric bimorph type vibrators, an offset voltage having an opposite phase is generated without fail between one vibrator and the other vibrator so as to create zero output. Accordingly, the circular direction vibrator according to the present invention can obtain a normal electric output only when a circular direction vibration is imparted to the vibrators.

When a predetermined voltage is applied to the pair of piezoelectric bimorph type vibrators, since the basic ends of the pair of piezoelectric bimorph type vibrators are secured to the carrier in a cantilever fashion, one vibrator is vibrated at its free end in one direction of thickness and the other vibrator is vibrated at its free end in the other direction of thickness. In other words, a conversion of the electric energy into vibration in the opposite directions of thickness can be obtained easily and without fail. Accordingly, the present invention has such an advantage in that a favorable circular direction vibration is generated about the carrier member, thereby ensuring the transmission of the circular direction vibration and enabling an amplification of the circular direction vibration.

According to the present invention, the circular direction vibrator as mentioned above can be easily formed by a combination of known piezoelectric bimorph type vibrators, and its structure is very simple, and a circular direction vibration in a correct vibrating orbit can be obtained with a high degree of reliability.

Further, the circular direction vibrator is quite suitable as a vibrator in, for example, a viscosity meter or a density meter which employs the circular direction vibrating mode as a driving mode or a detecting mode. In comparison, if a conventional direction vibrator were used as a driving source in which the vibration thereof is transmitted to a detector, and the detector is vibrated in the same direction in the measuring liquid to detect the density or the viscosity of the liquid from changes in the vibration thereof, there are disadvantages such as a vibrating wave produced by the detector propagating in the measuring liquid to create wave motion which results in a disturbance. Therefore, a highly accurate measurement is difficult to obtain and the measuring range is limited. On the contrary, the above-mentioned circular direction vibrator overcomes these problems and can be suitably used as a driving source or a detecting source (vibration sensor) of a density meter or a viscosity meter.

Although the present invention has been described in its preferred form with a certain degree of particularity, it is understood that the present disclosure of the preferred embodiments has been made only in an illustrative manner and that numerous changes in the details of the structure and arrangement of the parts may be made without departing from the spirit and the scope of the present invention as hereinafter claimed.

What is claimed is:

1. A circular direction vibrator comprising:
    a support shaft;
    a carrier member integral with said support shaft; and
    a pair of vibrators each of which comprises a piezoelectric bimorph polarized such that the vibrator is capable of producing vibratory motion in a direction of thickness thereof when voltage is applied thereto,
    each of said vibrators having a fixed end mounted to said carrier member and a free end that is unrestrained in the vibrator so that each of said vibrators is supported by said carrier member in a cantilever manner,
    said vibrators extending from the fixed ends thereof in opposite directions from one another and symmetrically with respect to said support shaft, and
    the polarization directions of said vibrators oriented such that when vibration is transmitted to said vibrators through said support shaft in direction of rotation of said support shaft, said vibrators generate voltage having the same phase, while when voltage is applied to said vibrators, said vibrators produce vibrations acting in a circular direction corresponding to a direction of rotation of said support shaft and which vibrations are transmitted to said support shaft through said carrier member integral therewith.

2. A circular direction vibrator as claimed in claim 1, wherein said support member has a pair of opposite sides, and the fixed ends of said vibrators are each mounted to said carrier member at a respective one of said opposite sides and extend parallel thereto.

3. A circular direction vibrator as claimed in claim 1, wherein said pair of vibrators extend along a common linear line.

4. A circular direction vibrator as claimed in claim 1, wherein the free end of each of said vibrators comprises a mass having a predetermined moment of inertia.

* * * * *